United States Patent [19]
Lin et al.

[11] Patent Number: 5,883,268
[45] Date of Patent: Mar. 16, 1999

[54] PROCESS STREAM PURIFICATION

[75] Inventors: Shaw-Chan Lin, West Chester; Jeffery B. Danner, Kennet Square; John C. Jubin, Jr., West Chester, all of Pa.

[73] Assignee: Arco Chemical Technology, L.P., Greenville, Del.

[21] Appl. No.: 955,412

[22] Filed: Oct. 23, 1997

[51] Int. Cl.$^6$ .................................................. C07D 301/19
[52] U.S. Cl. .............................................................. 549/529
[58] Field of Search ............................................. 549/529

[56] References Cited

U.S. PATENT DOCUMENTS

| | | | |
|---|---|---|---|
| 3,351,635 | 11/1967 | Kollar | 260/348.5 |
| 3,439,001 | 5/1969 | Pell et al. | 549/500 |
| 4,066,706 | 1/1978 | Schmidt | 260/610 B |
| 4,186,085 | 1/1980 | Savage | 210/669 |
| 4,262,143 | 4/1981 | Bécker | 568/574 |
| 4,367,342 | 1/1983 | Wulff | 549/529 |
| 5,151,530 | 9/1992 | Marquis | 549/529 |
| 5,723,637 | 3/1998 | Tsuji et al. | 549/529 |

FOREIGN PATENT DOCUMENTS 2742150  6/1997  France .

OTHER PUBLICATIONS

Translation by Dutch Plant Permit Document Ebhp U–4100, U4200 Dec. 12, 1996.
Earhart, J.P. et al, Chem. Eng. Prog. 1977, 73(5), pp. 67–73.

*Primary Examiner*—John Kight
*Assistant Examiner*—Raymond Covington
*Attorney, Agent, or Firm*—William C. Long

[57] ABSTRACT

Ethylbenzene hydroperoxide suitable for epoxidizing an olefin using a heterogeneous titanium catalyst is provided by the sequence of:

a) flashing acids containing ethylbenzene peroxidase to reduce the temperature thereof to 170° F. or lower, b) contacting the flash bottoms with aqueous base and separating a base contaminated deacidified hydroperoxide stream from an organics contaminated aqueous stream, c) removing organics from the organics contaminated aqueous stream by extraction with ethylbenzene, d) separating base from the base contaminated deacidified hydroperoxide stream by water extraction, and e) stripping water from deacidified water extracted hydroperoxide stream.

6 Claims, 1 Drawing Sheet

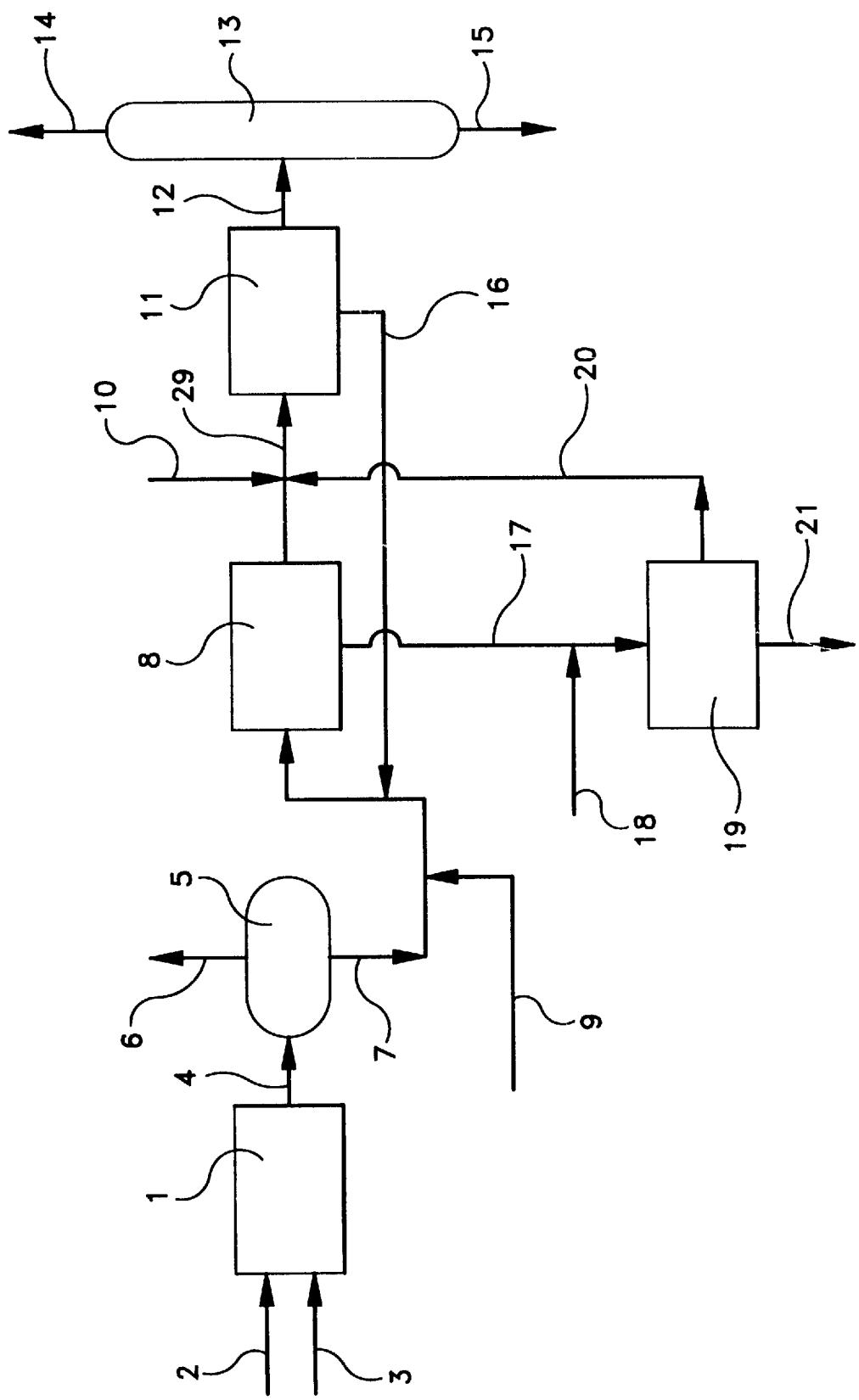

ved process
PROCESS STREAM PURIFICATION

FIELD OF INVENTION

The present invention relates to an improved process stream purification which is especially useful in an overall process for the epoxidation of an olefin using a solid heterogeneous catalyst containing titanium.

BACKGROUND OF THE INVENTION

The production of oxirane compounds such as propylene oxide by the catalytic reaction of an olefin and an organic hydroperoxide is a process of great importance which is practiced on a large scale in the industrial world. U.S. Pat. No. 3,351,635 is the basic patent covering this process.

In one version of the process, an insoluble solid heterogenous catalyst is used; see, for example, U.S. Pat. No. 4,367,342. A disadvantage of the use of the heterogeneous catalysts, as contrasted with the use of soluble homogeneous catalyst systems, has been the tendency for the solid catalyst to deactivate over time resulting in a loss both of productivity and reaction selectivity. A potential advantage of the use of the heterogeneous catalysts would be decreased problems associated with the disposal of metal containing waste streams.

The problems of solid catalyst deactivation, especially as they relate to high volume continuous commercial processes, have been the subject of extensive studies. It has been found that the production of a hydroperoxide such as ethyl benzene hydroperoxide which can be used in the solid heterogeneous catalyzed epoxidation of olefin can be improved by an aqueous base treatment whereby the process shows greatly reduced deactivation of the solid catalyst. However, the aqueous stream resulting from such treatment presents its own disposal problems; the present invention provides a treatment to remove impurities from such aqueous streams.

SUMMARY OF THE INVENTION

In the present process a hydroperoxide containing reaction mixture from a conventional peroxidation reaction is treated by a sequence of steps whereby the quality and suitability of the hydroperoxide for use in solid catalyzed epoxidations is substantially improved. Specifically, a peroxidation reaction product mixture, preferably after being rapidly cooled from the peroxidation reaction temperature to a temperature which is at least 20° C. lower than the peroxidation reaction temperature, and preferably to below 100° C., is contacted with aqueous base in amount sufficient to neutralize acidic components thereof and the resulting mixture is phase separated into separate aqueous and organic phases. The organic phase, which contains some base, is water washed to separate the basic materials and the resulting organic phase is stripped of water and can then advantageously be used in the solid catalyzed epoxidation of an olefin without the severe catalyst deactivation which results from the use of untreated peroxidate. The aqueous phase from the base treatment, in accordance with the invention, is contacted with hydrocarbon, eg. ethyl benzene in the case of the treatment of ethyl benzene hydroperoxide, in order to extract and remove organic contaminants from the aqueous phase, thus to improve the purity and ease of disposal of the aqueous phase.

DESCRIPTION OF THE DRAWING

The accompanying drawing illustrates in schematic form a practice of the invention.

DETAILED DESCRIPTION

The invention can best be described with reference to the accompanying drawing with application of the invention to the production of propylene oxide from propylene and ethyl benzene hydroperoxide.

Referring to the drawing, ethylbenzene and molecular oxygen are introduced into reactor 1 via lines 2 and 3 respectively and therein are reacted in accordance with known procedures to produce ethylbenzene hydroperoxide. U.S. Pat. No. 4,066,706 provides a description of this reaction and this description is incorporated herein by reference as is the description in U.S. Pat. No. 4,262,143.

The peroxidation reaction mixture, generally comprised of about 2 to 10 wt % ethylbenzene hydroperoxide and containing various acidic materials formed during the peroxidation, is removed from reactor 1 via line 4. Generally, this mixture is at the peroxidation reaction temperature of about 90° to 160° C. and peroxidation pressure of about 0 to 100 psig. At the peroxidation temperature there is a tendency for substantial decomposition of the hydroperoxide as a function of time.

Advantageously, the reaction mixture is passed via line 4 to flash drum 5 wherein pressure is reduced and a substantial portion of the reaction mixture, eg. 10–40% by weight, is flashed overhead and removed via line 6. The flashed material is primarily ethylbenzene and can be conveniently recycled to reactor 1 (not shown). As a result of the flashing, the temperature of the liquid bottoms in drum 5 is decreased somewhat, eg. to the region of 35° to 100° C. at which the hydroperoxide is reasonably stable.

The cooled bottoms from flash drum 5 which contains ethyl benzene hydroperoxide passes via line 7 to washing and separation zone 8. An aqueous stream containing a base such as sodium carbonate or sodium hydroxide passes via line 9 into line 7 where it is admixed with the cooled liquid bottoms from drum 5. Sufficient base is added via line 9 to provide a stoichiometric ratio of base to the acids contained in the cooled bottoms from drum 5 of at least about 1.0, preferably at least about 1.2 up to about 3. The bottoms and the aqueous base are thoroughly admixed and then phase separated in zone 8 into an upper hydroperoxide containing organic phase which is substantially reduced in acidic materials content as compared with untreated oxidate and a lower aqueous phase containing basic salts of the oxidate acids.

The organic phase is removed from zone 8 via line 29 and can be contacted with wash water which is introduced via line 10. The purpose of the water wash is to remove such basic materials as are in the hydroperoxide containing organic stream as a result of the base treatment. The organic and aqueous admixture passes to separation zone 11 wherein aqueous and organic phases are phase separated. The hydroperoxide containing organic phase substantially free of both organic acids and basic material passes via line 12 to distillation zone 13 where water contained therein is stripped overhead and removed via line 14. The bottoms stream is removed via line 15 and can be used as such or after concentration of the hydroperoxide by distillation (not shown) in an epoxidation reaction with propylene catalyzed by solid heterogeneous catalyst such as that shown in U.S. Pat. No. 4,367,342.

As a result of the above described process sequence greatly improved catalyst performance is achieved as compared with the use of hydroperoxide containing peroxidate not so treated, while at the same time hydroperoxide loss due to decomposition is kept to a minimum.

In a preferred practice, the aqueous phase from separation zone 11 can be recycled via line 16 to admixture in line 7 with the fresh base introduced via line 9 and the flash drum bottoms, thus providing an aqueous recycle.

In accordance with the invention, the aqueous phase is removed from zone 8 via line 17 and is admixed with ethylbenzene which is introduced via line 18. This mixture passes to separation zone 19 wherein it is phase separated. The purpose of this novel extractive contact is to separate organic materials from the aqueous phase; ethylbenzene stream containing the extracted organic materials can be passed via line 20 to admixture with the water and treated organic stream from zone 8. Generally, about 0.1 to 10 lbs of extracting hydrocarbon is used per lb of the aqueous phase from zone 8. Although ethylbenzene is preferred, other hydrocarbons such as cyclohexane, benzene, $C_6$–$C_{10}$ alkanes, and the like are also useful.

The purified aqueous stream is removed from zone 19 via line 21 and, because of its reduced organic impurity level, it can be discharged with but a minimum of further treatment.

The following example illustrates the invention.

Example

Referring to the drawing, ethylbenzene is reacted in reactor 1 with molecular oxygen to form ethylbenzene hydroperoxide at conventional reaction conditions of 125°–145° C. and 25–55 psig. The ethylbenzene is introduced into reactor 1 via line 2 and molecular oxygen via line 3.

The peroxidate reaction mixture stream is removed from reactor 1 via line 4, and passed via line 4 to flash drum 5. The pressure is reduced to about 130 mm Hg and a vapor stream mainly comprised of ethylbenzene is removed via line 6; the removed ethylbenzene may be recycled.

The flash drum bottoms stream now at 80° C. is removed from flash drum 5 via line 7. An aqueous sodium carbonate stream (25 wt % $Na_2 CO_3$ in water) is admixed via line 9 with this flash drum bottoms and to this mixture is added the recycle aqueous phase from separation zone 11 via line 16.

In separation zone 8 the mixture is phase separated into an upper organic phase and the lower aqueous phase. The organic phase is removed via line 29 and sent to wash zone 11.

The lower aqueous phase passes at the rate of 256 lbs/hr from separator 8 via line 17, the composition by weight being about 1.6% sodium carbonate, 11% organic acid salts, and 0.3% dissolved and entrained organic compounds. Ethylbenzene at the rate of 52 lbs/hr is introduced via line 18 and admixed with the aqueous phase from separation zone 8. The resulting mixture is phase separated in separation zone 19 into an upper organic phase comprised by weight of 98.5% ethylbenzene and 1.5% extracted organics and this phase is removed from zone 19 via line 20 at the rate of 52 lbs/hr.

The aqueous phase from zone 19 is removed at the rate of 256 lbs/hr via line 21 and can be disposed of by conventional means. The composition by weight of this phase is 1.6% sodium carbonate, 11% organic acid salts and 0.06% others.

The organic phase from separation zone 19 is passed via line 20 to admixture with the organic phase from separation zone 8 and with wash water introduced via line 10 and the resulting mixture is phase separated in separation zone 11 into an upper organic phase which is substantially free of base and a lower aqueous phase. The lower aqueous phase comprised by weight of about 1–3% sodium compounds passes at the rate of 178 lbs/hr via line 16 to admixture with the aqueous sodium carbonate and flash drum bottoms as above described.

The organic phase passes from zone 11 via line 12 to distillation zone 13 wherein water is stripped overhead.

The bottoms stream is removed from distillation zone 13 via line 15. This stream comprises by weight ethylbenzene hydroperoxide, and ethylbenzene and can be used to great advantage in the catalytic epoxidation of propylene to form propylene oxide using a solid heterogeneous titanium containing catalyst. For example, a typical tabulation of epoxidation conversion and selectivity as a function of time using the above treated ethylbenzene hydroperoxide is compared in the following table with comparable results with untreated ethylbenzene peroxidate. Selectivity and conversion are based on hydroperoxide.

TABLE

|  | Run Time, hours | % Selectivity Difference | Reaction Rate |
|---|---|---|---|
| Untreated hydroperoxide | 200 | 0 | 1.0 |
|  | 500 | −3.0 | 0.4 |
| Treated hydroperoxide | 200 | +4.0 | 2.0 |
|  | 500 | +3.0 | 1.5 |

We claim:

1. In a method for obtaining a purified ethyl benzene hydroperoxide stream useful for the solid heterogeneous catalyst catalyzed reaction with propylene to form propylene oxide wherein (a) a crude ethyl benzene hydroperoxide stream obtained by peroxidation of ethyl benzene optionally after flash distillation, is contacted with an aqueous solution of an alkali metal base and the resulting mixture is separated into an aqueous stream and a deacidified organic stream, and (b) the deacidified organic stream is contacted with water and the resulting mixture separated into an organic-contaminated water phase and an organic phase having a reduced alkali metal content as compared to the deacidified organic stream; the improvement which comprises:

(c) contacting the said organic-contaminated water phase with an extractive hydrocarbon selected from ethyl benzene, benzene, cyclohexane, and $C_2$–$C_{10}$ alkanes, and separating the resulting mixture into a purified water phase having a reduced level of organic contaminants as compared to the organic-contaminated water phase and a organic phase comprised of said extractive hydrocarbon and organic impurities from the organic-contaminated water phase.

2. The method of claim 1 wherein the organic-contaminated water phase is extracted with ethyl benzene.

3. The method of claim 1 wherein the organic-contaminated water phase is extracted with benzene.

4. The method of claim 1 wherein the organic-contaminated water phase is extracted with cyclohexane.

5. The method of claim 1 wherein the organic-contaminated water phase is extracted with 0.1 to 10 lbs of extractive hydrocarbon per lb. of water phase.

6. The method of claim 1 wherein the aqueous solution of an alkali metal base is an aqueous solution of sodium carbonate.

* * * * *